United States Patent
Heismann et al.

(10) Patent No.: US 9,259,171 B2
(45) Date of Patent: Feb. 16, 2016

(54) MAGNETIC RESONANCE DEVICE

(75) Inventors: Björn Heismann, Erlangen (DE);
Sebastian Schmidt, Weisendorf (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 707 days.

(21) Appl. No.: 13/551,857

(22) Filed: Jul. 18, 2012

(65) Prior Publication Data
US 2013/0021034 A1 Jan. 24, 2013

(30) Foreign Application Priority Data
Jul. 19, 2011 (DE) .......................... 10 2011 079 383

(51) Int. Cl.
*A61B 5/055* (2006.01)
*A61B 5/00* (2006.01)

(52) U.S. Cl.
CPC ............... *A61B 5/0555* (2013.01); *A61B 5/742* (2013.01)

(58) Field of Classification Search
CPC ............................... A61B 5/742; A61B 5/0555
See application file for complete search history.

(56) References Cited

U.S. PATENT DOCUMENTS

| 5,134,373 | A | * | 7/1992 | Tsuruno et al. ................. 324/309 |
| 5,150,710 | A | * | 9/1992 | Hall et al. ...................... 600/422 |
| 5,339,813 | A | * | 8/1994 | DeYoe ................. A61B 5/0555 359/419 |
| 5,412,419 | A | | 5/1995 | Ziarati |
| 6,029,082 | A | * | 2/2000 | Srinivasan et al. ............. 600/422 |
| 6,433,548 | B1 | * | 8/2002 | Furuta et al. ................... 324/318 |
| 6,591,128 | B1 | * | 7/2003 | Wu .................... G01R 33/34084 324/318 |
| 6,693,427 | B2 | * | 2/2004 | Drobnitzky et al. ........... 324/318 |
| 6,774,929 | B1 | * | 8/2004 | Kopp ............................... 348/61 |
| 8,483,797 | B2 | * | 7/2013 | Hempel ......................... 600/418 |
| 8,866,480 | B2 | * | 10/2014 | Waffenschmidt .... G01R 33/283 324/318 |
| 2010/0238362 | A1 | | 9/2010 | Hughes |

FOREIGN PATENT DOCUMENTS

| CN | 1521681 A | 8/2004 |
| CN | 201387480 Y | 1/2010 |
| DE | 29905420 U1 | 7/1999 |
| DE | 202005021902 U1 | 4/2011 |
| JP | 2002102203 A | 4/2002 |
| WO | WO 0122108 A1 | 3/2001 |

OTHER PUBLICATIONS

Andrew Ian Rickard, GB-Oxford; Technik Report Band 99, veröffentlicht am May 26, 2011; Others; 2011.
Morneburg, Heinz: Bildgebende Systeme für die medizinische Diagnostik, 3. Auflage. Erlangen: Publicis MCD Verlag, 1995, S. 503, ISBN 3-89578-002-2; Book; 1995; DE.
2011J06927.

* cited by examiner

*Primary Examiner* — Dixomara Vargas

(57) ABSTRACT

A magnetic resonance device having a tunnel for accommodating a patient is disclosed. The magnetic resonance device has a lining which clads both the tunnel and the end faces adjacent to it. At least one OLED, LCD or LED display panel is movably disposed on or in the lining cladding the tunnel or the lining cladding the end face. The display panel disposed in the tunnel is disposed on a bracket which can travel linearly along the lining and/or along the circumference of the lining. The display panel disposed on the end-face lining can travel and/or be tilted vertically.

8 Claims, 2 Drawing Sheets

MAGNETIC RESONANCE DEVICE

CROSS REFERENCE TO RELATED APPLICATIONS

This application claims priority of German application No. 10 2011 079 383.6 filed Jul. 19, 2011, which is incorporated by reference herein in its entirety.

FIELD OF INVENTION

The application relates to a magnetic resonance device having a tunnel for accommodating a patient as well as a lining which clads both the tunnel and the end faces adjacent thereto.

BACKGROUND OF INVENTION

Although examinations using magnetic resonance devices produce excellent image results, they are unpleasant, and sometimes intolerable, for a good many groups of patients. Mention can be made for claustrophobic patients, elderly patients and children. The main factor in this sensitivity and in the adverse reaction on the part of a patient to an unpleasant feeling, which depending on its nature can result in the scan in progress being aborted, is the small distance between the eyes and the lining, such as in the case of patients introduced into the tunnel head first during the relatively long time they must remain prone. The result is a feeling of a narrow enclosed space and of being shut in. Additionally, a good many patients are unable to lie still for a lengthy period or undertake certain activities for a lengthy period, for example calm, constant breathing, which is chiefly observed to be the case with small children, who frequently do not manage to keep still for a lengthy period without external incentives. Boredom is also a primary factor with children. Head examinations, which are very frequently performed, are especially awkward, as the head is then positioned in the isocenter of the magnet, and consequently is introduced deep into the tunnel as far as the middle, if necessary linked to a connected head coil. The feeling of "being shut in" is at its strongest as a result.

Various solutions are known for providing patients with audio-visual impressions and thereby distracting and occupying them for the duration of the measurement. Spectacles with built-in image sources are mostly used for this purpose, or permanently built-in tilted mirrors with an associated, external television set which can be watched via the tilted mirror. Headphones are also sometimes used. A drawback of the currently available solutions however is that they are relatively expensive or the image impression is very unsatisfactory. Tilted mirrors or spectacles restrict the field of vision in an unnatural way, are frequently uncomfortable to wear or reinforce the feeling of enclosure. An externally positioned television set to be watched by way of a tilted mirror must be specially designed to be MR-compatible in view of the magnetic fields prevailing in the vicinity of the device, which makes it very expensive. The same applies for the special spectacles.

A magnetic resonance device of the type described in the introduction is known for example from the book "Bildgebende Systeme für die medizinische Diagnostik" [Imaging Systems for Medical Diagnostics], 3rd edition, 1995, page 503, by Heinz Morneburg.

From U.S. Pat. No. 5,412,419 a magnetic resonance device is known in which a vertically suspended display is provided in the interior of the tunnel. The prone patient can see the display by way of a tilted mirror.

From DE 20 2005 021 902 U1 a magnetic resonance tomography system is known with a movable laser in the interior of the tunnel, said laser being used to mark an injection site on the patient to take a tissue sample, in other words to perform a biopsy.

From DE 299 05 420 U1 a bracket is further known for a heavy device to be fixed to a wall or ceiling, such as a television set, a monitor, a loudspeaker or a camera.

Finally, from US 2010/0238362 A1 it is known to place video spectacles on the patient while he is in a magnetic resonance device, in order to display information directly to him via the spectacles.

SUMMARY OF INVENTION

The object of the application is therefore to specify a magnetic resonance device which represents an improvement on these.

This object is achieved with a magnetic resonance device, whereby at least one OLED, LCD or LED display panel is disposed on or in the lining.

In the case of the disclosed magnetic resonance device just one display panel comprising an MR-compatible display matrix is disposed on or in the lining. Suitable for such an MR-compatible display matrix is an OLED panel, but an LCD or LED panel is also suitable. Because only the display panel is built in, which is flat and only has a narrow holding frame with associated operating electronics as appropriate, it is possible to build the display panel directly onto or into the lining, in other words virtually flush. As a result it is possible for this display panel, which because it is merely intended to transmit distracting audio-visual information does not need to be all that big, to be built in virtually on a user-defined basis, because as described it can be optimally integrated into the lining.

The display panel can here be disposed fixed to the lining cladding the tunnel or to the lining cladding the end face. Obviously it is conceivable to build in such a display panel both in the tunnel and on the end face in each case. By way of the display panel in the tunnel, for example an OLED panel, it is possible to convey impressions to the patient and distract him even if he is introduced head first. If the head is located outside the tunnel, he can be provided with information via the panel integrated onto the end face.

Whereas the alternative to the application described previously relates to the fixed panel arrangement, an alternative to this is obviously also to dispose the display panel movably in or on the lining cladding the tunnel or the lining cladding the end face. This embodiment of the application enables the display panel to be adjusted appropriately, and thus consequently enables its position to be adapted optimally to the position of the patient's head. If for example a head scan is to be performed, the panel disposed in the tunnel and mounted on a corresponding guide or bracket can be moved lengthways into the corresponding position. If the head is instead located at the start of the tunnel, the panel can be moved into this position. In the case of an end-face arrangement it is conceivable to position the panel so that it can tilt for example, so that ultimately it can be pivoted as required between a vertical and a horizontal position. The horizontal position is adopted if the patent's head is positioned near to the entrance of the tunnel; if the head is further outside, the display panel is set up. Obviously it is also possible to position the display panel on the end face so that the height can be adjusted vertically.

The display panel disposed in the tunnel is disposed on a bracket which is disposed so that it can travel linearly along the lining and/or can travel along the circumference of the lining. This bracket, designed as a type of slide, can be moved on corresponding rails embodied on the lining which can for example be embodied integrally by corresponding shaping of the lining which is generally made of plastic, so that simple lengthways guidance is ensured. In a corresponding fashion the lining disposed on the end face can travel vertically by way of such a bracket, on which it can also be disposed, as described, so as to tilt.

Expediently the display panel is automatically moved in a controlled fashion using an operating unit. To this end a suitable drive is provided, for example a small integrated motor or similar, in order to move the bracket, the movement being effected by way of a corresponding operating unit, for example provided externally to the device, or an operating unit activated by the patient himself. Automatic tilting can also be effected in a corresponding fashion. Obviously once again all components required for the automatic movement or tilting are again designed to be MR-compatible.

Although in principle the option exists for the display panel—where it is disposed externally to the tunnel—to communicate with a signal and/or energy supply unit via wires, it is however for the display panel to communicate wirelessly with the external signal and/or energy supply unit. This is expedient when the display panel is disposed on the side of the tunnel, since as described there is little room available there for routing supply cables.

Furthermore an external signal transmission unit can be provided with an associated selection unit, which can be operated by the patient introduced into the tunnel, to select information content to be displayed, which is stored in a memory of the signal transmission unit. This means that the signal transmission unit, which is disposed externally, possesses a corresponding memory in which for example selectable movies or other information content are stored. The patient can select these at will if he can activate the corresponding operating unit. Obviously it is of course also conceivable for desired information content to be selected by a person operating the system.

Furthermore a microphone or an operating element can be assigned in the display panel for interaction with the patient. Using this, the patient, to whom corresponding voice commands are of course also given via the display panel or loudspeakers or headphones associated therewith, can communicate quasi-interactively with an external person or can perform certain actions using voice control, for example speak certain words during head examinations, or perform certain movements, or, if he has to keep in a certain position, give corresponding activation signals to indicate that he has adopted it, etc. This means that genuine interaction can take place in this way. Corresponding interaction can of course also take place via a corresponding operating element, for example a button, for example if the patient is asked to assume a certain position. By pressing the button he can then give the activation signal that he has performed this.

Finally it can be provided that an optical unit associated with the patient can be used to compensate for poor eyesight on the part of a patient, such as in the form of spectacles or a lens element, exchangeable if necessary, disposed on a head coil to be worn in connection with an examination. In this way it is possible to compensate for the relatively small distance to the monitor for patients with poor eyesight. Whereas for people with normal eyesight, such as children, there is no problem in focusing on a point on the interior of the tunnel, this is sometimes not always possible for older adults (presbyopia, inability to focus on objects close up). This can be achieved by using either spectacles set up to be MR-compatible or a corresponding (focusing) lens between eye and display, which is built into a head coil.

BRIEF DESCRIPTION OF THE DRAWINGS

Further features and details of the application will emerge from the embodiment described below and with the aid of the drawing. This shows.

DETAILED DESCRIPTION OF INVENTION

Figure 1:
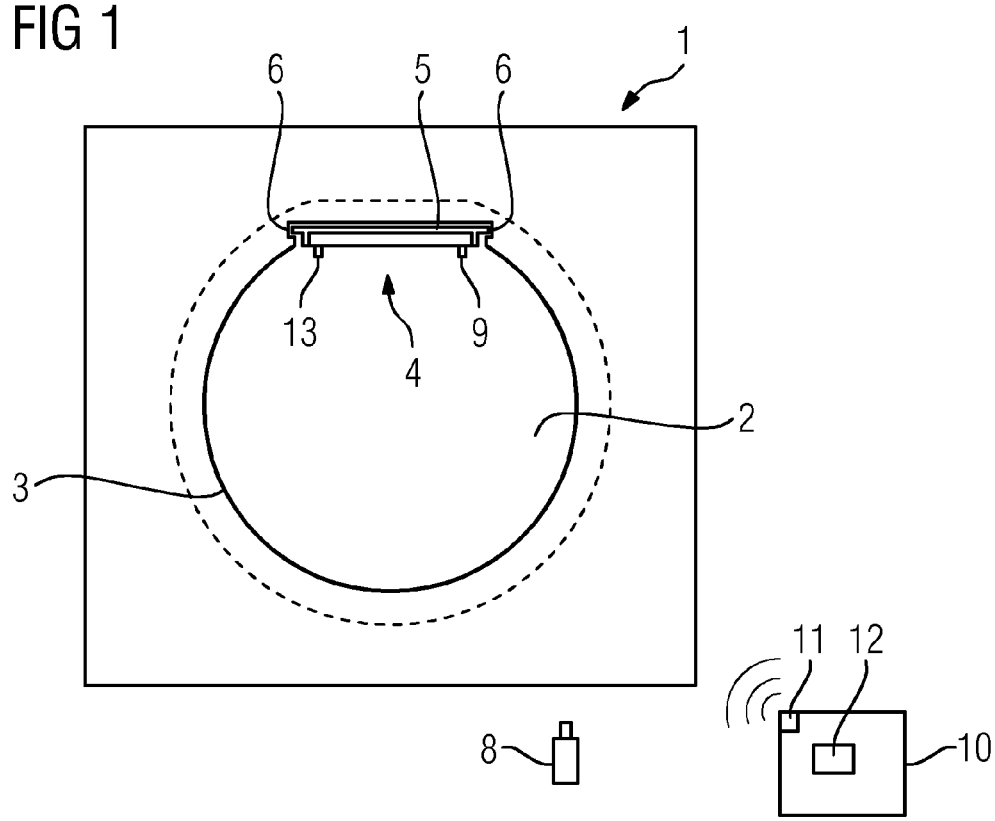
FIG. 1 a front view of a disclosed magnetic resonance device, shown only partially, FIG. 2 a sectional view through the magnetic resonance device from FIG. 1, FIG. 3 a front view of a further disclosed magnetic resonance device, and FIG. 4 a side view of the magnetic resonance device from FIG. 3.

FIG. 1 shows a disclosed magnetic resonance device 1, comprising, obviously in addition to other standard components, a tunnel 2, which is clad with a lining 3. A display panel 4, such as an OLED display panel, is disposed on or in this lining, integrated so as to travel along the axis of the tunnel. The display panel used here is a flat one which because of its OLED design is MR-compatible. The display panel 4 is disposed on a suitable bracket 5, which is accommodated in corresponding guide rails 6 extending axially and embodied on the lining 3 or can be guided and moved lengthways therein. The bracket 5, obviously made of MR-compatible material, is set up to be as simple as possible, as ultimately it merely serves to fix and linearly guide the display panel 4.

Figure 2:
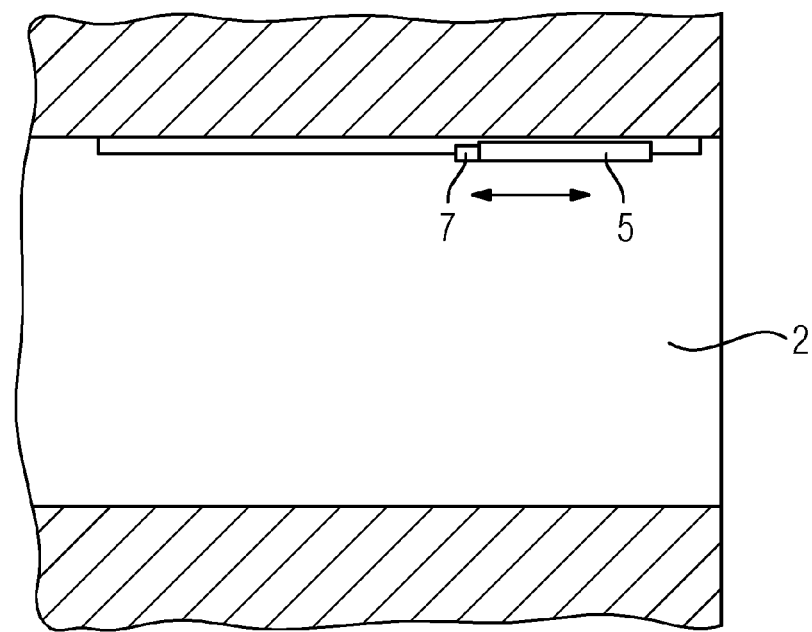

The positioning of the display panel 4 or the bracket 5 along the tunnel 2 can either be performed simply by moving it manually, or it is also conceivable for this to be done automatically, for which purpose, see FIG. 2, a motor 7 which performs the automatic movement is disposed on the bracket 5, so that the bracket 5, as shown by the double arrow, can be moved in both directions. Control can be effected for example using a small handheld transmitter 8, which either the patient himself can activate or which can also be activated by a person external to the device who is performing the examination.

Also associated with the display panel 6 is a transceiver unit 9 which wirelessly transmits signals relating to the information content to be displayed on the display panel and/or wirelessly transmits energy. This transceiver 9 communicates with an external signal and/or energy transmission unit 10 which of course possesses its own transmission and/or receiving unit 11, as well as a memory 12 in which for example selectable information content to be displayed such as short movies or similar is stored. The desired information content can again be selected by the patient for example, where appropriate using the handheld transmitter 8, or else by a person performing the examination. In each case the display panel 4 shown in FIG. 1 is accommodated without cables in the tunnel. Power can also be supplied to the motor 7 in this way where appropriate.

Furthermore an audio unit 13 is provided, which can either be just a loudspeaker, just a microphone, or a corresponding combination of these. The patient can be given instructions via a loudspeaker, providing he is not wearing headphones already fitted with one. The patient can engage quasi-interactively with the external environment and keep in contact via a microphone. For example, he can, if he has previously received an instruction to assume a certain position or to perform certain corresponding actions, signal that he has assumed the position or has started the action. The voice signal is captured via the microphone 13 and is transmitted externally via the signal transmission unit 9. Overall therefore a certain communication can take place between the patient and the person performing the examination in this way.

Figure 3:
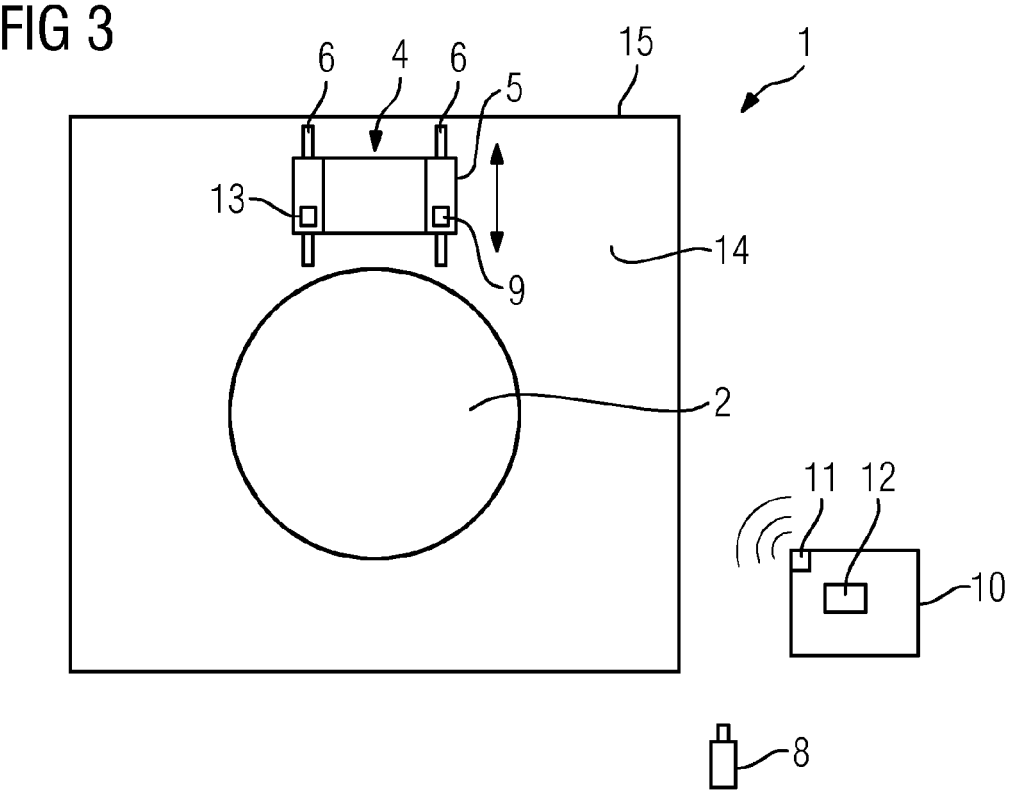
Figure 4:
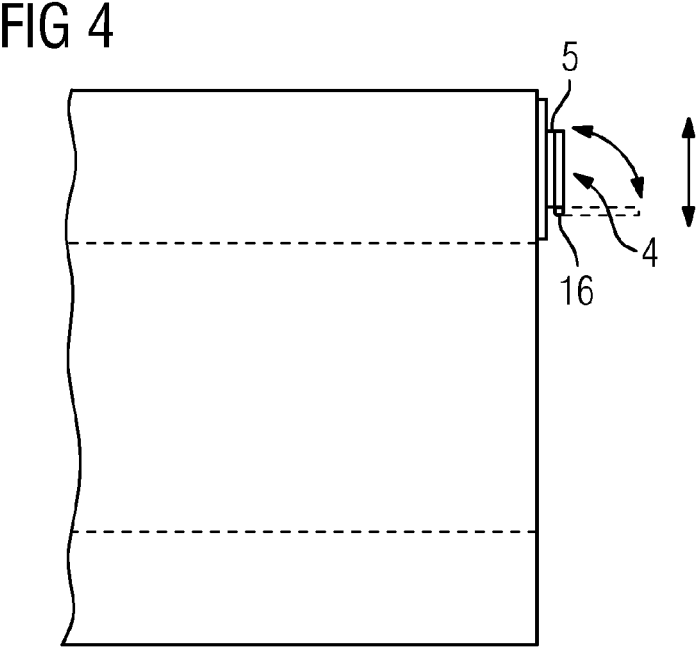

A further embodiment of a disclosed magnetic resonance device 1 is shown in FIG. 3, wherein the same reference characters are used for the same components. Again provided here is a tunnel 2 and a lining 15 cladding the end face 14, on which in this embodiment the display panel 4, such as an OLED panel because it is insensitive to MR, is disposed. The display panel is again located on a bracket 5 which can also be moved vertically here on corresponding guide rails 6 which are embodied directly and integrally on the lining 15 made of plastic (the same of course applies as regards the plastic lining 3), as is shown by the double arrow. The vertical movement can again be effected manually or by a motor not shown here in greater detail. The transceiver unit 9 for transmitting signals and/or for supplying energy is again associated with the display panel, as is the unit 13, be it a loudspeaker, a microphone or both. Information content can be conveyed to the patient by way of this display panel 4 if he is disposed with his head outside the tunnel 2. The further away he is, the simpler it is to view the vertically disposed display panel 4. However, in order to permit an optimum panel alignment relative to the patient's head, the display panel 4, see FIG. 4, is disposed on the bracket 5 so as to pivot about an axis of rotation 16, in order to pivot the display panel 4, as shown by the double arrow, out of the vertical position into the horizontal position. This means that patients whose head is disposed immediately adjacent to the entrance to the tunnel can also thereby be optimally provided with distracting information by way of the horizontally pivoted display panel. The movement control of the bracket 5, where this can travel and/or be tilted automatically, is again effected for example via the handheld transmitter 8, which in this disclosed embodiment too can be designed as an operating element for the patient to give interactive signals to the person performing the examination.

A combination of the two embodiments shown is of course also possible, so that the magnetic resonance device has both a display panel disposed in the tunnel and one disposed outside the tunnel.

Although the application has been illustrated and described in greater detail using the embodiment, the application is not restricted to the examples disclosed and other variations can be derived from by the person skilled in the art, without exceeding the scope of protection of the application.

The invention claimed is:

1. A magnetic resonance device, comprising:
   a tunnel for accommodating a patient;
   a lining that clads the tunnel and an end face adjacent to the tunnel;
   a bracket disposed on the lining that travels along the tunnel; and
   a display panel disposed on the bracket that travel along the tunnel and is guided by the bracket.

2. The magnetic resonance device as claimed in claim 1, further comprising an operating unit that controls the display panel to automatically travel and/or be tilted.

3. The magnetic resonance device as claimed in claim 1, wherein the display panel wirelessly communicates with an external signal transmission unit and/or an external energy supply unit.

4. The magnetic resonance device as claimed in claim 3, wherein the external signal transmission unit comprises a selection unit for selecting information stored in a memory of the external signal transmission unit for display by the patient in the tunnel.

5. The magnetic resonance device as claimed in claim 1, wherein the display panel comprises a microphone or an operating element for interaction with the patient.

6. The magnetic resonance device as claimed in claim 1, further comprising an optical unit to compensate eyesight of the patient.

7. The magnetic resonance device as claimed in claim 6, wherein the optical unit comprises a spectacle or a lens element disposed on a head coil to be worn by the patient.

8. The magnetic resonance device as claimed in claim 1, wherein the display panel comprises an OLED, LCD or LED.

* * * * *